United States Patent [19]

Recknor et al.

[11] Patent Number: 5,667,657
[45] Date of Patent: Sep. 16, 1997

[54] PRESSURE INJECTION APPARATUS AND METHOD FOR INJECTING A SAMPLE INTO AN ELECTROPHORESIS CAPILLARY

[75] Inventors: Michael William Recknor, Oakland; David A. Wolze, San Jose, both of Calif.

[73] Assignee: Dionex Corporation, Sunnyvale, Calif.

[21] Appl. No.: 535,539

[22] Filed: Sep. 28, 1995

[51] Int. Cl.[6] .................... G01N 27/26; G01N 27/447
[52] U.S. Cl. .................................. 204/604; 204/453
[58] Field of Search ................................ 204/604, 453, 204/602; 137/115

[56] References Cited

U.S. PATENT DOCUMENTS

| | | | |
|---|---|---|---|
| 5,207,886 | 5/1993 | Lauer et al. | 204/299 R |
| 5,217,590 | 6/1993 | Lauer et al. | 204/180.1 |
| 5,240,578 | 8/1993 | Tatsumi | 204/604 X |
| 5,358,613 | 10/1994 | Schneider et al. | 204/604 X |

FOREIGN PATENT DOCUMENTS 0 339781  3/1989  European Pat. Off. .

OTHER PUBLICATIONS

Lauer, H.H., et al., "Prince: A Variable Pressure Injection Device for Modular CE–Systems." Lauer Labs BV, Kapitein Nemostraat 16A, 7821 AC Emmen, Netherlamds. no date available.

Primary Examiner—Kathryn L. Gorgos
Assistant Examiner—John S. Starsiak, Jr.
Attorney, Agent, or Firm—Flehr, Hohbach Test Albritton & Herbert

[57] ABSTRACT

A present invention and method provides a pressure injection apparatus (20) that injects a quantitatively defined volume of liquid sample (21) from a container (22) into a capillary device (23). A servo pressure primary regulator (26) is included which precisely regulates the fluid from a supply pressure ($P_S$) to a substantially constant regulated pressure ($P_R$) in communication with the liquid sample (21) for a predetermined period of time. A feedback mechanism cooperates with a valving assembly (31) to continuously monitor and adjust the regulated pressure ($P_R$) to be substantially constant and precise for delivery to the container (21).

79 Claims, 2 Drawing Sheets

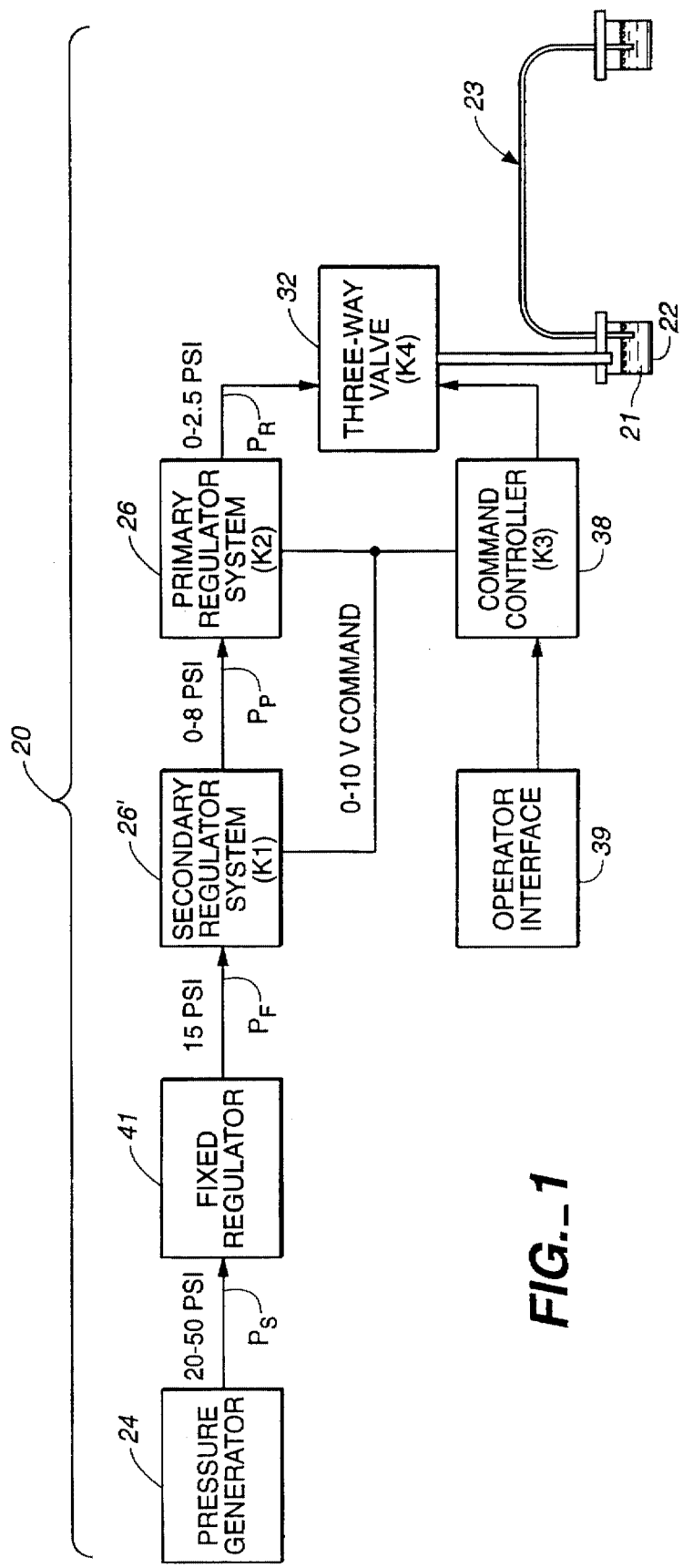
FIG._1

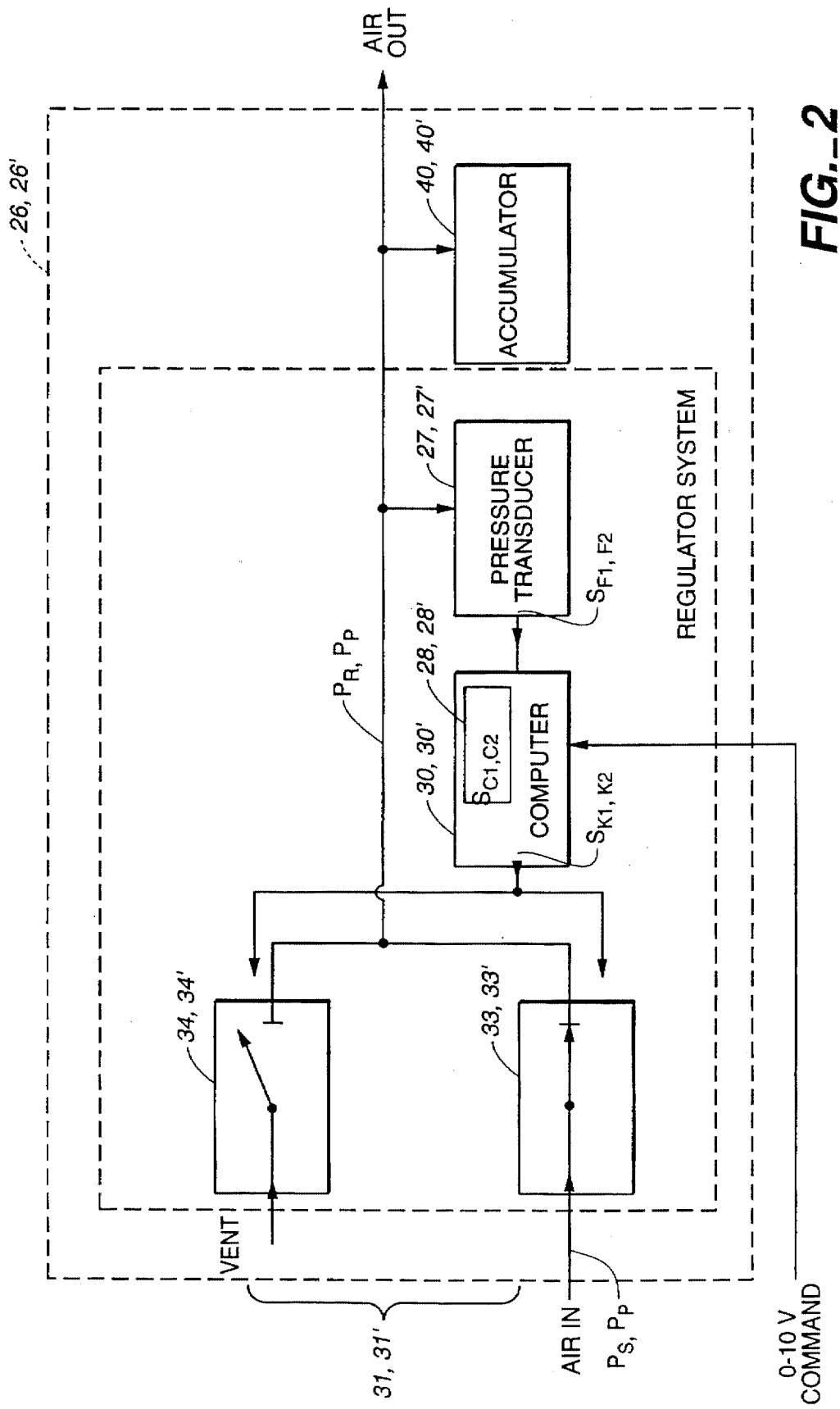
FIG._2

PRESSURE INJECTION APPARATUS AND METHOD FOR INJECTING A SAMPLE INTO AN ELECTROPHORESIS CAPILLARY

TECHNICAL FIELD

The present invention relates, generally, to capillary electrophoresis, and more particularly, relates to a pressure injection apparatus for reproducibly injecting a liquid sample into an electrophoresis capillary tube.

BACKGROUND ART

In recent years, significant advances have been made in micro-column separation techniques, such as capillary electrophoresis (CE). Injecting a precise and reproducible volume is fundamental to any separation technique. The volume reproducibility of injection is generally expected to be less than two percent, and is often required to be less than one percent to be analytically useful. This task is especially difficult in CE due to the extremely small volumes reproduced, as well as the frequent employment of narrow-bore capillary columns having inner diameters less than 100 μm.

In capillary electrophoresis, injection of the samples usually requires that the inlet end of the separation capillary be removed from the electrolyte vial and installed in the sample vial. The liquid sample analyte is subsequently moved from the sample vial into the source end of the capillary, either by applying pressure to the sample vial and forcing the liquid into the end of the capillary or by applying a voltage differential between the sample solution, the destination vial, and across the capillary. This voltage differential electrokinetically drives the ionic analytes into the end of the capillary. The inlet end of the separation capillary is then removed from the sample vial and reinstalled in the inlet electrolyte vial.

In electrokinetic injection or electromigration, an end of the capillary and an electrode are placed into the sample and a voltage is briefly applied, causing a small band of sample to electromigrate into the capillary. This technique is generally reliable, and only depends on reproducible viscosity of the sample solution, reasonably constant ionic strength of the sample, and reproducible applied voltage. While all these requirements are reasonable to achieve, this technique of sample injection suffers from discrimination within the sample because solutes or analyte ions with higher mobilities will preferentially migrate into the electrophoresis column, and therefore change the relative composition of the sample.

Accordingly, pressure injection techniques or controlled pressure differentials over the separation column may be preferred in many instances. Generally, pressure injection has been induced either by gravity flow or siphoning, or by applying a constant vacuum or overpressure to the source or destination end of the connecting column.

In the gravity injection method, the source end of the capillary and the sample vial are positioned at controlled differential heights above the destination end of the capillary such that gravity forces the sample liquid into the capillary at a controlled rate.

While this technique is generally reproducible in many situations, this method is problematic when applied to extremely small volumes, such as those employed in capillary electrophoresis. In these instances, the surface forces between the sample fluids and the capillary walls and reservoir walls have a greater adverse affect on the relatively small injected volumes.

Moreover, in gravity injection, the inlet end of the capillary must be capable of being moved relative the outlet end to use gravity to force the liquid into the capillary. However, more recent CE instrument designs employ cassette assemblies to support and mount the capillary. While these cassette assemblies effectively isolate the capillary to improve the necessary temperature control, the inlet end must be fixed relative to the outlet end which essentially eliminates gravity injection as an optional mode.

In the overpressure or vacuum technique, a number of parameters must be reproducible with a relatively high tolerance to achieve the required injection accuracy and reproducibility. In addition to a reliable seal, and a reproducible volume sample-to-sample, the injection pressure applied to the sample vial must be reproducible to within at least 0.1 psi while the time that pressure is applied must be reproducible to within at least 0.1 seconds. Moreover, the viscosity of the liquid sample must be reproducible, sample-to-sample, as well. Typical of these patented pressure injection devices may be found in U.S. Pat. Nos. 5,207,886; 5,217,590 to Lauer et al.; and European Patent Application Publication No. 0,339,781 A2 to Burolla.

The Burolla system calculates the intended injection volume by measuring the pressure and time parameters during the injection, and then integrating the pressure-time curve. Hence, by determining the length of injection time required, at the applied real-time pressure, the intended volume injected into the capillary can be accurately estimated.

This system is advantageous in that the absolute pressure applied need not be accurately controlled, since the pressure is being measured real-time and since the time necessary to achieve the required injected volume can be varied, real-time, according to the actual pressure applied. Hence, during pressure fluctuations and undulations inherent in these systems, the length of time of the applied pressure can be varied to compensate for these fluctuations. This technique is capable of achieving reproducible injections with a Relative Standard Deviation (RSD) of less than two (2) percent.

One problem associated with these arrangements, however, is a potential lack of correlation between the actual volume injected and the estimated intended volume injected when very small injection volumes are concerned. The dynamic gain of the Beckman system is very high relative to very small injection volumes. In combination with the electronic and mechanical delays of the system, pressure fluctuations substantially decrease the volumetric accuracy for small volumes. Further, the relatively slow ramp-up times of pressure applied to the pressurized fluids and/or pressure fluctuations can cause variation in the dynamics of the sample injection process, which in turn adversely affect the accuracy and precision of the injected volumes.

In the Lauer system, the overpressure is applied to the inlet end of one of three capillary configurations to inject the liquid sample therein. U.S. Pat. No. 5,207,886 describes an injection device having a vacuum at the capillary outlet to perform the injection, while U.S. Pat. No. 5,217,590 discloses an injection system formed to apply overpressure in either a forward or rearward direction. In either system, a piston system is employed to generate the required pressure.

While this assembly is potentially very accurate, it is susceptible to system pressure leaks. This leakage is primarily caused by the repetitive sealing and unsealing at the sealed sample vials during handling which eventually deteriorates the seal integrity. Since the actual applied pressure is not measured or accounted for, even a small leak deleteriously affects the vial pressure causing variations in the actual injection volume, injection to injection.

DISCLOSURE OF INVENTION

Accordingly, it is an object of the present invention to provide a pressure injection apparatus and method that accurately injects a quantitatively defined volume of liquid sample from a sample vial into a capillary device for capillary electrophoresis.

Another object of the present invention is to provide a capillary electrophoresis pressure injection apparatus and method which applies substantially constant and precise injection pressure to the liquid sample in the sample vial or container.

Still another object of the present invention is to provide a capillary electrophoresis pressure injection apparatus and method which maintains injection accuracy regardless of minor pressure leaks between the injection apparatus and the sample vial for a selected period of time.

Yet another object of the present invention is to provide a capillary electrophoresis pressure injection apparatus and method which is volumetrically reproducible.

Another object of the present invention is to provide a capillary electrophoresis pressure injection apparatus and method which substantially improves transient response.

It is a further object of the present invention to provide a capillary electrophoresis pressure injection apparatus and method which is durable, compact, easy to maintain, has a minimum number of components, and is easy to use by unskilled personnel.

In accordance with the foregoing objects, the present invention provides a pressure injection apparatus that injects a quantitatively defined volume of liquid sample from a container into a capillary device. The pressure injection apparatus includes a supply source of pressurized fluid at a supply pressure to urge the liquid sample into the inlet of the capillary device. Further, the injection apparatus include a servo pressure primary regulator and a distributor device. The primary regulator is coupled in series between an output of the supply source and the inlet of the capillary device, and precisely regulates the fluid from the supply pressure to a substantially constant regulated pressure for a selected period of time. The distribution device, coupled to an output of the primary regulator, selectively distributes the fluid at the substantially constant and precisely regulated pressure to the container.

More particularly, the servo pressure regulator includes a pressure sensor outputting a feedback signal proportional to real time measurement of the regulated pressure, and a reference source outputting a command signal having a value representing a predetermined command pressure. The servo regulator further includes a computer coupled to receive as inputs the feedback signal and the command signal, and outputs a compensation signal in response to a difference between the first feedback signal and the second command signal. A valving assembly, responsive to the compensation signal and in communication with the fluid, is formed to adjust the regulated pressure to be substantially equal to the command pressure such that a magnitude of the difference is reduced.

Accordingly, the computer of the servo regulator receives the command signal and the feedback signal, and in response controls the valving assembly to maintain the output pressure of the servo pressure regulator at a substantially constant and precise commanded value.

The valving assembly includes a vent valve responsive to the compensation signal, and controllably movable between a closed position and an opened position. In the opened position, the vent valve controllably vents the fluid to reduce the regulated pressure thereof. The valving assembly further includes an inlet valve responsive to the compensation signal which is controllably movable between a shut position condition and an unshut position. In the unshut position, the inlet valve enables communication of the fluid at the supply pressure with the fluid at the regulated pressure to increase the regulated pressure.

The servo pressure primary regulator of the present invention preferably includes an accumulator having an internal reservoir in fluid communication with the distribution device at the regulated pressure. The accumulator substantially reduces fluctuations caused by the valving action of the servo pressure regulator assembly. It also regulates the dynamic response of the servo, providing stability of operation.

To further improve the delivery of constant pressure to the container by the injection apparatus, a secondary high range servo pressure regulator is included cascaded with, and in upstream communication with, the primary regulator. This additional servo regulator works in tandem with the primary servo regulator to improve the performance thereof. Preferably, the gain of the secondary regulator, from a command voltage to the preregulated pressure, is substantially proportional to the primary gain of the primary regulator, from the command voltage to the regulated pressure. This enables the secondary regulator to track the primary regulator to provide a substantially constant ratio between the preregulated pressure and the regulated pressure.

A method for injecting a quantitatively defined volume of liquid sample from a container into a capillary device is included comprising the steps of: a) generating a pressurized fluid at a supply pressure; b) regulating the fluid from the supply pressure to a precise, substantially constant regulated pressure through a servo pressure primary regulator. This step is accomplished by 1) outputting a first feedback signal, from a pressure sensor, proportional to real time measurement of the regulated pressure, 2) outputting a second command signal, from a first reference source, having a value representing a predetermined first command pressure, 3) comparing the first feedback signal and the first command signal through a first computer, and outputting a first compensation signal in response to a difference between the first feedback signal and the second command signal, and 4) precisely adjusting the regulated pressure, through a valving assembly responsive to the first compensation signal and in communication with the fluid, to be substantially equal to the command pressure such that a magnitude of the difference is reduced. The method further includes the step of c) selectively exposing the liquid sample contained in the container to the fluid at the substantially constant and precise regulated pressure for a predetermined period of time to inject the defined volume of the liquid sample from the container into the capillary device.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 1 is a schematic of a pressure injection apparatus constructed in accordance with the present invention.

FIG. 2 is a schematic of a servo pressure regulator of the pressure injection apparatus of FIG. 1.

DETAILED DESCRIPTION OF THE INVENTION

While the present invention will be described with reference to a specific embodiment, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Attention is now directed to FIG. 1 where the pressure injection apparatus, generally designated 20, is schematically illustrated for injecting a quantitatively defined volume of liquid sample 21 from a container or sample vial 22 into a capillary device 23. The pressure injection apparatus includes a pressure generator or supply source 24 of pressurized fluid, typically a gas, at a supply pressure ($P_S$) used to urge liquid sample 21 into an inlet of capillary device 23. A servo pressure primary regulator, generally designated 26, is coupled in-series between an output of supply source 24 and an inlet of capillary device 23 and regulates the fluid from the supply pressure ($P_S$) to a substantially constant and precisely controlled regulated pressure ($P_R$). A distribution device 23, coupled to an output of primary regulator 26, selectively distributes the fluid to the container 22 at the substantially constant and precisely regulated pressure ($P_R$).

Accordingly, a pressure injection apparatus for capillary electrophoresis is provided including a servo pressure regulator with a feedback loop mechanism. This arrangement enables continuous and near instantaneous microadjustments of the regulated fluid to maintain a substantially constant regulated pressure for a selected period of time with a precision unattainable with the current prior art pressure injection apparatus which employ fixed spring-type pressure regulators. By providing rapid, continuous microadjustments to maintain the regulated fluid at the commanded pressure, to be delivered to the sample vial at a substantially constant pressure at all times during the selected time period, and by accurately controlling the actuation time of the distribution device 32, the volumetric accuracy and precision of the sample liquid injected into the capillary is dramatically increased. Hence, the injection patterns can be varied (i.e., at a first substantially constant pressure for the first selected period of time, and subsequently, at a second substantially constant pressure for a second selected period of time, etc.).

In the preferred embodiment, primary regulator 26 includes a pressure sensor 27 outputting a first feedback signal ($S_{F1}$), proportional to the real time measurement of the regulated pressure ($P_R$), and a reference source 28 outputting a first command signal ($S_{C1}$) having a value representing a predetermined target command output pressure. The command output pressure represents the desired output pressure (i.e., regulated pressure) to be delivered from the primary servo regulator to the sample vial, as commanded by the user for the selected period of time.

As best shown in FIG. 2, primary servo regulator 26 further includes a computer 30 coupled to receive as inputs first feedback signal ($S_{F1}$) and first command signal ($S_{C1}$). Subsequently, computer 30 outputs a first compensation signal ($S_{K1}$) in response to a difference between the first feedback signal and the first command signal. A valving assembly, generally designated 31, is included, responsive to the compensation signal ($S_{K1}$), which provides an interface between the supply fluid at the supply pressure and regulated fluid at the regulated pressure. The valving assembly adjusts the output regulated pressure ($P_R$) in response to the operator's command to be substantially equal to the command pressure such that a magnitude of the difference between the feedback signal and the command signal is reduced. Distribution device 32, in fluid communication with the output of primary regulator 26, then selectively distributes the fluid at the commanded substantially constant regulated pressure to container 22 for precisely the period of time selected by the operator.

The servo pressure regulator of the present invention continuously measures the output regulated pressure ($P_R$) of the fluid and compares it to the desired or target command pressure, through computer 30, to determine if the measured regulated pressure is above, below or substantially equivalent to the command pressure value. Subsequently, if the value of the regulated pressure is not equivalent to the command pressure value (i.e., outside deadband region of the computer), the valving assembly 31 is actuated to adjust the regulated fluid to either increase or decrease the regulated pressure until that value is substantially equivalent to the command pressure value (i.e., within the deadband region). Thus, using the valving assembly 31 as the actuator in a servo-loop, and the pressure transducer 27 as a feedback device, the air flow and pressure can be electronically manipulated to deliver substantially constant air pressure to the sample vial. By further controlling the distribution device 32, the present invention creates pressure-time waveforms for reproducible sample injections which give the operator active control over the process.

Hence, the present invention compensates for pressure measurement inaccuracies or drift that are inherent in the fixed spring-type air pressure regulators.

Further, the cavity pressure of prior art fixed air pressure regulators do not increase as a step function to instantaneously deliver the regulator pressure to the sample vial, but rather must be ramped-up which causes further volumetric calculation inaccuracies. Additionally, for small injections, prior art injection systems used operating pressures that were too high, necessitating short timing periods and resulting in poor system dynamics.

By accurately controlling the regulated pressure at the distribution device so as to be substantially constant, the pressure ramp is nearly a true step function where the fluid is distributed at the regulated and substantially constant pressure, relatively near instantaneously. Further, by accurately controlling the actuation time of the distribution device 32, the volumetric accuracy of the sample liquid injected into the capillary is dramatically increased. As will be apparent below, reproducible injection volumes having Relative Standard Deviations (RSD) of less than 0.2% are attainable through use of the present invention.

Incidently, when the output pressure falls within the deadband region, as mentioned, the computer closes both valves in valve assembly to maintain pressure stability. The preferred deadband width is between about ±0.001 psi to about ±0.005 psi (most preferably ±0.001 psi) relative the target command pressure. When the difference between the command pressure and the regulated pressure is preferably less than about ±0.001 psi, the valve assembly is closed relative the venting to the atmosphere or in fluid communication with the fluid at the supply pressure. Hence, hysteresis halts or suspends any subsequent increasing or decreasing adjustments, through the valving assembly, to the regulated pressure in this deadband space.

One important advantage of this arrangement is that the pressure injection system is more tolerant to the adverse affects of pressure leaks. In the event of minor system pressure leaks, especially at the sample vial/manifold seals which generally cause volumetric calculation inaccuracies, servo pressure regulator 26 will automatically compensate for the leak by manipulating the regulated fluid to still be delivered to sample vial 22 at a substantially constant injection pressure.

Referring now to FIG. 2, first valving assembly 31 is schematically represented which includes an inlet valve 33 coupled between pressure generating assembly 24 and sample vial 22. Inlet valve 33 provides controlled fluid communication between the pressurized supply fluid, from pressure generating assembly 24 at the supply pressure ($P_S$), and the regulated fluid at the regulated pressure ($P_R$) delivered to sample vial 22. Since the supply pressure ($P_S$) is generally greater than the regulated pressure ($P_R$), the regulated pressure can be increased by controlling passage and communication between the two fluids, via inlet valve 33. Hence, in the event the measured regulated pressure drops below the target command pressure, inlet valve 33 can be opened until the regulated pressure is equivalent to or surpasses the command pressure.

Similarly, first valving assembly 31 includes a vent valve 34 positioned in-line or in fluid communication with the regulated fluid at the regulated pressure ($P_R$) to provide system venting thereof. In the event the measured regulated pressure surpasses the command pressure, vent valve 34 can be controllably opened to vent system fluid into the atmosphere until the regulated pressure is equivalent to or drops below the command pressure.

The inlet valve and vent valve are preferably two-way precision valving devices designed for the electronic manipulation of air flow and pressure. In the preferred embodiment, these valves are rapid response, milliwatt range proportional valves or silicon microvalves such as the digitally controlled microvalves provided Proportion-Air, Inc. and Mac, Inc., or the analog controlled microvalves provided by Redwood Micro Systems.

Each valve 33, 34 is electrically coupled to a computer 30 which includes a valve controller portion for actuation thereof between an opened position and a closed position for the vent valve, and an unshut position and a shut position for the inlet valve. Briefly, in the opened position, the vent valve vents the regulated fluid from the servo regulator to decrease the regulated pressure, while in the unshut position, the inlet valve provides communication between the supply fluid at the supply pressure with the regulated fluid to increase the regulated pressure. In the preferred form, the vent valve and the inlet valve will never be in the opened position and the unshut position, respectively, at the same moment.

As set forth above, servo pressure regulator 26 provides a feedback mechanism which continuously monitors and micro-adjusts the regulated fluid pressure. This feedback mechanism includes a pressure sensor 27 positioned downstream from the valves to measure the pressure of the regulated fluid (i.e., the regulated pressure ($P_R$)). Pressure sensor 27 is preferably implemented by a pressure transducer which outputs first feedback signal ($S_{F1}$) which may be proportional to the real time measurement of the regulated pressure. This first feedback signal is input into computer 30 which then compares the first feedback signal ($S_{F1}$) to the first command signal ($S_{C1}$). The first command signal is of a value representing the target command pressure selected by the operator.

Upon a positive or negative difference being measured between the first feedback signal and the second command signal, which falls outside the deadband region and which may be proportional to the positive or negative difference between regulated pressure and the command pressure, the computer 30 outputs the first command signal ($S_{C1}$) which also may be proportional to that first difference. In response, computer 30 energizes either vent valve 34 to the opened position or inlet valve 33 to the unshut position, depending upon whether the measured regulated pressure is above or below the target command pressure, respectively. This arrangement enables a precisely controlled, substantially constant pressure at the distribution device 32 for the designated period of time. Hence, this improved precision results in substantially increased volumetric accuracy of sample liquid injected into the capillary.

As best viewed in the schematic of FIG. 1, distribution device 32 selectively distributes the regulated fluid at the regulated pressure to sample vial 22, and mates with sample vial in a manner forming a seal. Distribution device 32 preferably includes a three-way solenoid valve which provides fluid communication between servo pressure regulator 26 and the sample vial when energized. When de-energized, the three-way valve (not schematically represented) seals output of servo pressure regulator 26, and vents the sample vial to the atmosphere.

A central command controller 38 electrically couples the servo pressure regulator 26 to distribution device 32 for active control of computer 30 and the timing control of the three-way valve of the pressure injection apparatus. Further, an operator interface 39 is provided coupled to command controller 38 to control the voltage output thereof for the selected periods of time.

In accordance with the present invention, valving assembly 31 may be either analog or digitally controlled. An analog controlled system is advantageous in that the regulated pressure has less ripple. The primary disadvantage, however, is that the analog controlled systems are slower responding to pressure variations and changes, especially upon initial delivery of the regulated fluid to the sample vial. The analog controlled valves may be advantageous partially opened or closed, in proportion to the differences measured between the input and output pressures of the regulator. Digital controlled valves, on the other hand, can only be either fully opened or fully closed.

To improve the response time, stabilize the servo, and smooth the pressure ripple, the servo pressure regulator 26 includes an accumulator (FIG. 2), generally designated 40, which provides a reservoir of regulated fluid at the regulated pressure between the valving assembly 31 and distribution device 32. By providing a reservoir of pressurized fluid, the injection apparatus is capable of a fast pressure ramp when the distribution device three-way valve is initially commanded to connect the accumulator to sample vial 22 subsequent to operation and stabilization of the servo pressure regulator at the desired command pressure. Further, the reservoir of regulated fluid provides a buffer zone which acts to stabilize the output of the servo pressure regulator caused by the servo action.

To disconnect and vent sample vial 22 from the regulated pressure to atmospheric pressure, vent valve 34 is de-energized to be opened. Similarly, upward ramping can be minimized by first stabilizing the servo pressure regulator at the target command pressure prior to energizing the distribution device three-way valve to open and provide communication between the servo pressure regulator and the sample vial.

While the present servo pressure regulator is capable of directly receiving the supply fluid at the supply pressure, too large a pressure reduction between the supply pressure and the regulated fluid at the regulated pressure (i.e., approximately the target command pressure) can be detrimental to the pressure regulators. Hence, in the preferred form and as shown FIG. 1, a fixed spring-type regulator assembly 41, is included between pressure generating assembly 24 and secondary regulator 26'. Fixed regulator assembly 41 is initially employed to reduce the supply pressure as well as reduce the relatively large fluctuations caused by the pressure generator.

This reduction of the supply pressure to a lower generally constant pressure ($P_F$) is similar in characteristic and precision to those fixed regulators provided in the prior art pressure injection assemblies. Hence, the fixed regulated fluid provided by fixed regulator assembly 41 also tends to drift, and is slow responding to the primary servo regulator requirements.

It has been found beneficial to further preregulate the supply fluid after the fluid passes through the fixed pressure regulator. This arrangement is beneficial in that the secondary regulator tracks the first regulator, maintaining the ratio of inlet to outlet pressure on the primary regulator. Maintenance of this ratio greatly improves the repeatability and accuracy of the primary regulator.

Accordingly, a servo pressure secondary regulator assembly, generally designated 26' in FIG. 1, and related secondary accumulator 40', are cascaded with servo pressure primary regulator 26 between fixed regulator assembly 41 and the primary servo regulator. Servo pressure secondary regulator 26' is preferably structurally identical to the servo pressure primary regulator schematically represented in FIG. 2. Hence, the secondary regulator 26' includes a secondary inlet valve 33', a secondary vent valve 34', a secondary pressure transducer 27' and a secondary computer 30'. Moreover, secondary regulator 26' functions in a similar feedback manner to continuously monitor and adjust the preregulated fluid pressure. This feedback mechanism positions the secondary pressure sensor or transducer downstream from the secondary inlet and vent valves 33', 34' to measure the pressure of the preregulated fluid (i.e., at the preregulated pressure ($P_P$)). The secondary pressure transducer 27' which outputs a second feedback signal ($S_3$) proportional to the real time measurement of the regulated pressure. This second feedback signal is input into the secondary computer 30' which then compares the second feedback signal to a second command signal ($S_4$). The second command signal is output from a secondary reference source 28', and is of a value representing the secondary target command pressure.

Similar to the primary regulator, upon a positive or negative difference being measured between the second feedback signal and the second command signal, which may be proportionate to the positive or negative difference between preregulated pressure and the secondary command pressure, the secondary computer outputs a command signal ($S_{C2}$) which also may be proportional to that difference, should that difference fall outside the predetermined deadband space. In response, secondary computer 30' energizes either secondary vent valve 34' to the opened condition or the secondary inlet valve 33' to the unshut condition, depending upon whether the measured preregulated pressure is above or below the secondary target command pressure, respectively.

Accordingly, the supply fluid provided by pressure generating assembly 24, at supply pressure ($P_S$) of preferably twenty (20) to fifty (50) psi, passes through fixed regulator assembly 41 where the supply fluid is regulated to a generally constant pressure ($P_F$) of about fifteen (15) psi. Subsequently, this fixed regulated fluid communicates with secondary regulator 26' to regulate the fixed regulated fluid at a generally constant pressure to a substantially constant preregulated pressure ($P_P$) of between about zero (0) to about eight (8) psi, depending upon the desired target regulated pressure ($P_R$). Lastly, the preregulated fluid of secondary regulator 26' is in fluid communication with primary servo regulator 26 which regulates the preregulated fluid from a precisely controlled, substantially constant preregulated pressure ($P_P$) to a precisely controlled, substantially constant regulated pressure ($P_R$) of between about zero (0) to about two and one-half (2.5) psi. It will be understood, however, that these pressure values may be altered without departing from the true spirit and nature of the present invention.

The forward path gain (i.e., the regulated pressure reduction) of each servo pressure regulator is a function of the cross-sectional inlet area of each valve, the internal volume of the accumulator, and the ratio between the inlet and outlet pressures. If the gain is too high, the output pressure will tend to be unstable. In contrast, if the servo gain is too low, the response time will be too slow to be effective. Accordingly, it is highly advantageous to maintain the servo gain of each servo pressure regulator at a substantially constant value.

In accordance with the present invention, the secondary gain of secondary regulator 26', from a command voltage to preregulated pressure ($P_P$), is substantially proportional to the primary gain of primary regulator 26, from the command voltage to the regulated pressure ($P_R$). Hence, the secondary regulator tracks the primary regulator to provide a substantially constant ratio between the preregulated pressure and the regulated pressure. This enables the system to maintain good linearity in the rise and fall times.

This is preferably accomplished by each servo pressure regulator 26, 26' receiving the same input command voltage from central command controller 38. This is advantageous in that the two regulators track each other, maintaining the primary servo gain at a substantially constant value. Accordingly, the secondary regulator 26', at a 10 volt command voltage, is full-scaled to provide eight (8) psi; while the primary regulator 26, at a 10 volt command voltage, is full-scaled to provide two and one-half (2.5) psi. Proportionately, the secondary regulator 26', at a 5 volt command voltage, is scaled to provide four psi; while the primary regulator 26, at a 5 volt command voltage, is scaled to provide one and one-quarter (1.25) psi.

In the preferred form, the primary accumulator 40 includes an internal reservoir having a volume of at least one (1) cubic inch (and preferably three (3) cubic inches), while the secondary accumulator 40' includes an internal cavity having a volume of at least one (1) cubic inch (and preferably two (2) cubic inches). Further, in each servo pressure regulator, the ratio between the input to output pressure is preferably between about 2:1 to about 3:1. It will be appreciated that these values may vary without departing from the true spirit and nature of the present invention.

From the description of the present apparatus, it will be understood that a method for injecting a quantitatively defined volume of liquid sample from a container into a capillary device 23 is provided comprising the steps of: a) generating a pressurized fluid at a supply pressure ($P_S$); and b) regulating the fluid from the supply pressure to a substantially constant regulated pressure ($P_R$), for a selected period of time, through servo pressure primary regulator 26. The primary servo regulator regulates the supply fluid by 1) outputting a first feedback signal ($S_{F1}$), from pressure sensor 27, proportional to real time measurement of the regulated pressure, 2) outputting a first command signal ($S_{C1}$), from reference source 28, having a value representing a predetermined command pressure ($P_C$). The supply fluid is further regulated by 3) comparing the first feedback signal ($S_{F1}$) and the first command signal ($S_{C1}$) through computer, and outputting a compensation signal ($S_{K1}$) in response to a difference between the first feedback signal and the second command signal, and 4) adjusting the regulated pressure ($P_R$), through valving assembly 31 responsive to the compensation signal ($S_{K1}$) and in communication with the fluid, to be substantially equal to the command pressure such that a magnitude of the compensation signal is reduced. The method further includes the step of c) selectively exposing the liquid sample 21 contained in the container or sample vial 22 to the regulated fluid at the substantially constant and precisely regulated pressure ($P_R$) for a predetermined period of time to inject the defined volume of the liquid sample from container 22 into capillary device 23.

Moreover, the method may further include the step of, after the supplying step and before the regulating step, d) preregulating the fluid from the supply pressure to a precisely controlled, substantially constant preregulated pressure through a servo pressure secondary regulator 26'. This step may be accomplished by 1) outputting a second feedback signal ($S_3$), from a secondary pressure sensor 27', proportional to real time measurement of the preregulated pressure ($P_P$), and 2) outputting a second command signal ($S_4$), from a secondary reference source 28', having a value representing a predetermined second command pressure. Next, 3) comparing the second feedback signal and fourth the second command signal through a second computer 30', and outputting a second compensation signal ($S_{K2}$), proportional to a difference between the second feedback signal and the second command signal, and 4) adjusting the preregulated pressure ($P_P$), through a secondary valving assembly 31' responsive to the second compensation signal and in communication with the fluid, to be substantially equal to the second command pressure such that a magnitude of the second compensation signal is reduced.

The preregulating step includes the step of tracking the secondary gain of the secondary regulator, from the supply pressure to preregulated pressure, to be substantially proportional to the primary gain of the primary regulator, from the preregulated pressure to the regulated pressure. This enables a substantially constant ratio between the preregulated pressure and the regulated pressure to maintain good linearity in the rise and fall times.

The method may further include the step of, after the regulating step and before the exposing step, stabilizing the fluid at the regulated pressure through primary accumulator 40 having an internal reservoir at the substantially constant regulated pressure ($P_R$).

The following example serves to more fully describe the manner of using the above-described invention, as well as to set forth the best mode contemplated for carrying out various aspects of the invention. It is to be understood that this example in no way serves to limit the true scope of the invention, but rather are presented for illustrative purposes.

EXAMPLE 1

Reproducibility of Introduction of Sample Fluid into a Capillary for Capillary Electrophoresis The pressure injection system of the present invention was coupled to a typical capillary electrophoresis assembly including a sealed 4 ml sample vial containing sample solution. An inlet end of a 75 μm ID capillary tube, 50 cm in length, was submersed in the sample solution in the sample vial; while an opposite exit end was submersed in a buffer solution in an exit vial. A pressure transducer (strain gauge SynSim) was coupled to the sample vial to measure the regulated pressure pulse delivered to the sample vial from the present invention pressure injection system. An absorbance detector (DIONEXAD-20), mounted near the exit end of the capillary, monitored the sample fluid injected into the capillary, during capillary electrophoresis, to measure the component separation.

The present invention delivered a controlled pressure pulse of about 0.5 psi for about 5 seconds (i.e., 2.5 psi-sec.). Each capillary electrophoresis test was reproduced five times using a four component sample solution of Nicotinamide, Acetyl-Salicylic acid, p-hydroxy Benzoic acid, and Benzoic acid. The general electrophoresis procedure follows published procedures for capillary electrophoresis separation of ionic components in a buffer solution.

The area calculated under the curves for the pressure component is proportional to the total amount of pressure delivered to the sample solution during for the 5 second period; while the area calculated under the curves for each solution component is proportional to the total volume of sample component separated from the solution. These area units are provided in arbitrary units.

TABLE 1

| Component | Average Area | Variance Area | Relative Standard Deviation |
|---|---|---|---|
| Pressure | $3.106 \times 10^8$ | $1.472 \times 10^{11}$ | 0.12% |
| Nicotinamide | $7.266 \times 10^4$ | $1.996 \times 10^6$ | 1.94% |
| Acetyl Salicylic acid | $1.495 \times 10^4$ | $3.287 \times 10^4$ | 1.21% |
| p-hydroxy Benzoic acid | $2.323 \times 10^5$ | $2.869 \times 10^6$ | 0.73% |
| Benzoic acid | $1.435 \times 10^5$ | $6.854 \times 10^5$ | 0.58% |

What is claimed is:

1. A capillary electrophoresis pressure injection apparatus comprising:

a container containing liquid sample therein;

a capillary device formed for receiving a quantitatively defined volume of liquid sample, coupled to said container;

a supply source of pressurized fluid at a supply pressure to urge said liquid sample into an input of said capillary device;

a fixed pressure regulator, coupled in series to an output of supply source, that regulates said fluid at said supply pressure to a generally constant pressure;

a servo pressure secondary regulator, coupled in series to an output of fixed pressure regulator, that precisely regulates said fluid from said generally constant pressure to a substantially constant preregulated pressure for a selected period of time;

a servo pressure primary regulator, coupled in series to an output of secondary regulator, to further precisely regulate said fluid from said substantially constant preregulated pressure to a substantially constant regulated pressure for said selected period of time; and a distribution device, coupled to an output of said primary regulator, selectively distributing said fluid at said substantially constant and precisely regulated pressure to said container;

a primary accumulator, coupled in series between the output of said primary regulator and an input of said distribution device, having an internal reservoir at said substantially constant regulated pressure; and a secondary accumulator, coupled in series between the output of said secondary regulator and an input of said primary regulator, having an internal cavity at said substantially constant preregulated pressure.

2. The pressure injection apparatus as defined in claim 1 wherein, the secondary gain of said secondary regulator, from a command voltage to preregulated pressure, is substantially proportional to the primary gain of said primary regulator, from said command voltage to said regulated pressure such that said secondary regulator tracks said primary regulator to enable a substantially constant ratio between said preregulated pressure and said regulated pressure.

3. The pressure injection apparatus as defined in claim 2 wherein, said internal reservoir has a volume of at least 1 cubic inch, and said internal cavity has a volume of at least 1 cubic inch.

4. The pressure injection apparatus as defined in claim 2 further including:

a command controller operably coupled to said first computer and said second computer, and outputting a control signal thereto to maintain said second gain substantially proportional to said primary gain.

5. The pressure injection apparatus as defined in claim 4 wherein, said substantially constant ratio is about 3:1.

6. A method for injecting a quantitatively defied volume of liquid sample from a container into a capillary device comprising the steps of:

supplying a pressurized fluid at a supply pressure;

precisely regulating said fluid from said supply pressure to a substantially constant predetermined first command pressure through a servo pressure primary regulator by adjusting the regulated pressure regulated by said primary regulator toward said first command pressure only when the regulated pressure deviates from a deadband region corresponding to said first command pressure; and selectively exposing said liquid sample contained in skid container to said fluid at said substantially constant and precisely regulated pressure for a predetermined period of time to inject the defined volume of said liquid sample from said container into said capillary device.

7. The method as defined in claim 6 wherein, said regulating step is accomplished by:

outputting a first feedback signal, from a pressure sensor, proportional to real time measurement of the regulated pressure;

outputting a first command signal, from a first reference source, having a value representing said predetermined first command pressure;

comparing said first feedback signal and said first command signal through a first computer, and outputting a first compensation signal in response to a first difference between said first feedback signal and said first command signal; and adjusting said regulated pressure, through a valving assembly responsive to said first compensation signal and in communication with the fluid, to be substantially equal to said command pressure such that a magnitude of said first difference is reduced.

8. The method as defined in claim 7 further including the step of:

after said regulating step and before said exposing step, stabilizing said fluid at said regulated pressure through a primary accumulator having an internal reservoir at said substantially constant and precisely regulated pressure.

9. The method as defined in claim 6 further including the step of:

after said supplying step and before said regulating step, precisely preregulating said fluid from said supply pressure to a substantially constant preregulated pressure through a servo pressure secondary regulator for said predetermined period of time.

10. The method as defined in claim 9 wherein, said preregulating step is accomplished by:

outputting a second feedback signal, from a secondary pressure sensor, proportional to real time measurement of the preregulated pressure;

outputting a second command signal, from a secondary reference source, having a value representing a predetermined second command pressure;

comparing said second feedback signal and said second command signal through a second computer, and outputting a second compensation signal in response to a second difference between said second feedback signal and said second command signal; and adjusting said preregulated pressure, through a secondary valving assembly responsive to said second compensation signal and in communication with the fluid, to be substantially equal to said second command pressure such that a magnitude of said second difference is reduced.

11. The method as defined in claim 10 wherein, said preregulating step includes tracking the secondary gain of said secondary regulator, from a command voltage to preregulated pressure, to be substantially proportional to the primary gain of said primary regulator, from said command voltage to said regulated pressure to enable a substantially constant ratio between said preregulated pressure and said regulated pressure.

12. The method as defined in claim 6 further including the step of:

after said supplying step and before said regulating step, precisely preregulating said fluid from said supply pressure to a substantially constant predetermined second command pressure through a servo pressure secondary regulator by adjusting the preregulated pressure preregulated by said secondary regulator toward said second command pressure only when the preregulated pressure deviates from said second command pressure by a second predetermined amount.

13. The method as defined in claim 6 further including the step of:

after said supplying step and before said regulating step, generally regulating said fluid at said supply pressure to a generally constant pressure through a fixed pressure regulator.

14. The method as defined in claim 6 wherein:

said exposing step is accomplished by a distributor device enabling selective and substantially instantaneous communication of said fluid at said substantially constant and precisely regulated pressure with said container.

15. A method for injecting a quantitatively defined volume of liquid sample from a container into a capillary device comprising the steps of:

supplying a pressurized fluid at a supply pressure;

generally regulating said fluid at said supply pressure to a generally constant pressure through a fixed pressure regulator;

precisely regulating said fluid from said generally constant pressure to a substantially constant regulated pressure through a servo pressure primary regulator; and selectively exposing said liquid sample contained in said container to said fluid at said substantially constant and precisely regulated pressure for a predetermined period of time to inject the defined volume of said liquid sample from said container into said capillary device.

16. A pressure injection apparatus that injects a quantitatively defined volume of liquid sample from a container into a capillary device, said pressure injection apparatus comprising:

a container;

a capillary device;

a supply source of pressurized fluid at a supply pressure to urge said liquid sample into an input of said capillary device;

a fixed pressure regulator, coupled in series to said output of said supply source, that regulates said fluid at said supply pressure to a generally constant pressure;

a servo pressure primary regulator, coupled in series between an output of said fixed pressure regulator and an input of said capillary device, that precisely regulates said fluid from said supply pressure to a substantially constant regulated pressure for a selected period of time; and a distribution device, coupled to an output of said primary regulator, selectively distributing said fluid at said substantially constant and precisely regulated pressure to said container.

17. The pressure injection apparatus as defined in claim 16 wherein, said supply source is formed to output said supply pressure between about 20 psi and about 50 psi, said fixed pressure regulator is formed to regulate said generally constant pressure to between about 15 psi and about 25 psi, and said servo pressure primary regulator is formed to regulate said substantially constant regulated pressure to between about 0 psi and about 5 psi.

18. The pressure injection apparatus as defined in claim 16 wherein, said servo pressure primary regulator includes:

a first pressure sensor outputting a first feedback signal proportional to real time measurement of the regulated pressure;

a first reference source outputting a first command signal having a value representing a predetermined first command pressure;

a first computer coupled to receive as an input said first feedback signal, and outputting a first compensation signal in response to a first difference between said first feedback signal and said first command signal; and a first valving assembly, responsive to said first compensation signal and in communication with the fluid, formed to adjust said regulated pressure to be substantially equal to said first command pressure such that a magnitude of the first difference between said first feedback signal and said first command signal is reduced.

19. The pressure injection apparatus as defined in claim 18 wherein, a servo pressure secondary regulator, coupled in series between an output of said supply source and an input of said primary regulator, that precisely preregulates said fluid from said supply pressure to a substantially constant preregulated pressure supplied to said primary regulator, said secondary regulator including a second pressure sensor outputting a second feedback signal proportional to real time measurement of the preregulated pressure, a second reference source outputting a second command signal having a value representing a predetermined second command pressure, a second computer coupled to receive as inputs said second feedback signal and said second command signal, and outputting a second compensation signal in responsive to a second difference between said second feedback signal and said second command signal, and a second valving assembly, responsive to said second compensation signal and in communication with the fluid, formed to adjust said preregulated pressure to be substantially equal to said second command pressure such that a magnitude of said second difference signal is reduced.

20. The pressure injection apparatus as defined in claim 19 wherein, said first valving assembly includes a first vent valve responsive to said first compensation signal, and controllably movable between a closed position and an opened position, controllably venting the fluid in communication with said primary servo regulator to reduce said regulated pressure thereof, and a first inlet valve responsive to said first compensation signal, and controllably movable between a shut position and an unshut position, enabling communication of the at the preregulated pressure with the fluid at the regulated pressure to increase said regulated pressure thereof, and said second valving assembly includes a second vent valve responsive to said second compensation signal, and controllably movable between a closed condition and an opened condition, controllably venting the fluid to reduce said preregulated pressure thereof, and a second inlet valve responsive to said second compensation signal, and controllably movable between a shut condition and an unshut condition, enabling communication of the fluid at the supply pressure with the fluid at the preregulated pressure to increase said preregulated pressure thereof.

21. The pressure injection apparatus as defined in claim 20 wherein, said first computer further includes a first valve controller coupled to said first vent valve and said first inlet valve for controlled operation of said first vent valve between said closed position and said opened position, and of said first inlet valve between said shut position and said unshut position, and said second computer includes a second valve controller coupled to said second vent valve and said second inlet valve for controlled operation of said second vent valve between said closed condition and said opened condition, and of said first inlet valve between said shut condition and said unshut condition.

22. The pressure injection apparatus as defined in claim 21 wherein, said first vent valve, said first inlet valve, said second vent valve, and said second inlet valve are proportional microvalves.

23. The pressure injection apparatus as defined in claim 20 wherein, said first computer includes a first valve controller coupled to said first vent value and said first inlet valve for controlled operation of said first vent valve between said closed position and said opened position, and of said first inlet valve between said shut position and said unshut position;

said second computer further includes a second valve controller coupled to said second vent valve and said second inlet valve for controlled operation of said second vent valve between said closed condition and said opened condition, and of said second inlet valve between said shut condition and said unshut condition.

24. The pressure injection apparatus as defined in claim 23 further including:

a command controller operably coupled to said first computer and said second computer, and outputting a control signal for control of said first computer and said second computer simultaneously.

25. The pressure injection apparatus as defined in claim 24 further including:

a user interface coupled to said commend controller to selectively vary said control signal.

26. The pressure injection apparatus as defined in claim 24 wherein, said substantially constant ratio is between about 2:1 to about 3:1.

27. The pressure injection apparatus as defined in claim 18 wherein, said first valving assembly includes:

a first vent valve responsive to said first compensation signal, and controllably movable between a closed position and an opened position, controllably venting the fluid to reduce said regulated pressure thereof; and a first inlet valve responsive to said first compensation signal, and controllably movable between a shut position and an unshut position, enabling fluid communication of the fluid at the supply pressure with the fluid at the regulated pressure to increase said regulated pressure.

28. The pressure injection apparatus as defined in claim 27 wherein, said first computer includes a first valve controller coupled to said first vent valve end said first inlet valve for controlled operation of said first vent valve between said closed position and said opened position, and of said first inlet valve between said shut position said unshut position.

29. The pressure injection apparatus as defined in claim 28 wherein, said first vent valve and said first inlet valve are proportional microvalves.

30. The pressure injection apparatus as defined in claim 18 wherein, said first pressure sensor provided by is a pressure transducer.

31. The pressure injection apparatus as defined in claim 18 wherein, said first computer is configured to output said first compensation signal upon the absolute of said first difference between said first feedback signal and said first command signal must exceed a predetermined amount, representing a predetermined differential pressure, before said first computer outputs said first compensation signal forming a deadband space therebetween.

32. The pressure injection apparatus as defined in claim 31 wherein, said first computer is configured to output said first compensation when said predetermined differential pressure is between about 0.001 psi to about 0.005 psi.

33. The pressure injection apparatus as defined in claim 19 wherein, said first computer is configured to output said first compensation signal upon the absolute of said first difference between said first feedback signal and said first command signal exceeding a first predetermined amount, representing a first predetermined differential pressure, and said second computer is configured to output said second compensation signal upon the absolute of said second difference between said second feedback signal and said second command signal exceeding a second predetermined amount, representing a second predetermined differential pressure.

34. The pressure injection apparatus as defined in claim 33 wherein, said first computer is configured to output said first compensation signal when said first predetermined differential pressure is between about 0.001 psi to about 0.005 psi, and said second computer is configured to output said second compensation signal when said second predetermined differential pressure is between about 0.001 psi to about 0.005 psi.

35. The pressure injection apparatus as defined in claim 16 wherein, said primary regulator includes a primary accumulator, coupled in series between the output of said primary regulator and an input of said distribution device having an internal reservoir at said substantially constant regulated pressure.

36. The pressure injection apparatus as defined in claim 35 wherein, said internal reservoir has a volume of at least 1 cubic inch.

37. The pressure injection apparatus as defined in claim 16 further including:

a servo pressure secondary regulator, coupled in series between an output of said supply source and an input of said primary regulator, that precisely preregulates said fluid to a substantially constant preregulated pressure applied to said primary regulator for said selected period of time.

38. The pressure injection apparatus as defined in claim 37 wherein, the secondary gain of said secondary regulator, from a command voltage to preregulated pressure, is substantially proportional to the primary gain of said primary regulator, from said command voltage to said regulated pressure such that said secondary regulator tracks said primary regulator to enable a substantially constant ratio between said preregulated pressure and said regulated pressure.

39. The pressure injection apparatus as defined in claim 38 wherein, said secondary regulator includes:
- a second pressure sensor outputting a second feedback signal proportional to real time measurement of the preregulated pressure;
- a second reference source outputting a second command signal having a value representing a predetermined second command pressure;
- a second computer coupled to receive as inputs said second feedback signal and said second command signal, and outputting a second compensation signal in response to a second difference between said second feedback signal and said second command signal; and
- a second valving assembly, responsive to said second compensation signal and in communication with the fluid, and formed to adjust said preregulated pressure to be substantially equal to said second command pressure such that a magnitude of said second difference is reduced.

40. The pressure injection apparatus as defined in claim 32 further including:

digital control means operably connected to said primary and secondary regulators for digital operation thereof.

41. The pressure injection apparatus as defined in claim 31 further including:

analog control means operably coupled to said primary and secondary regulators for analog operation thereof.

42. The pressure injection apparatus as defined in claim 37 wherein, said secondary regulator includes:
- a second pressure sensor outputting a second feedback signal proportional to real time measurement of the preregulated pressure;
- a second reference source outputting a second command signal having a value representing a predetermined second command pressure;
- a second computer coupled to receive as inputs said second feedback signal and said second command signal, and outputting a second compensation signal in response to a second difference between said second feedback signal and said second command signal; and
- a second valving assembly, responsive to said second compensation signal and in communication with the fluid, and formed to adjust said preregulated pressure to be substantially equal to said second command pressure such that a magnitude of said second difference is reduced.

43. The pressure injection apparatus as defined in claim 37 wherein, said secondary regulator includes a secondary accumulator, coupled in series between the output of said secondary regulator and an input of said primary regulator, having an internal cavity at said substantially constant preregulated pressure.

44. The pressure injection apparatus as defined in claim 43 wherein, said internal reservoir has a volume of at least about 1 cubic inch, and said internal cavity has a volume of at least about 1 cubic inch.

45. The pressure injection apparatus as defined in claim 16 further including:

digital control means operably coupled to said primary regulator for digital operation thereof.

46. The pressure injection apparatus as defined in claim 16 further including:

analog control means operably coupled to said primary regulator for analog operation thereof.

47. The pressure injection apparatus as defined in claim 16 wherein, said distribution device includes a three-way valve device.

48. The pressure injection apparatus as defined in claim 16 wherein, said supply source is configured to output said supply pressure between about 20 psi and about 50 psi, said fixed pressure regulator is configured to regulate said generally constant pressure between about 15 psi and about 25 psi, and said servo pressure primary regulator is configured to regulate said substantially constant regulated pressure between about 0 psi and about 5 psi.

49. A pressure injection apparatus that injects a quantitatively defined volume of liquid sample from a container into a capillary device, said pressure injection apparatus comprising:

- a container;
- a capillary device;
- a supply source of pressurized fluid at a supply pressure to urge said liquid sample into an input of said capillary device;
- a servo pressure primary regulator, coupled in series between an output of said supply source and an input of said capillary device, that precisely regulates said fluid from said supply pressure to a substantially constant regulated pressure for a selected period of time;
- a servo pressure secondary regulator, coupled in series between an output of said supply source and an input of said primary regulator, that precisely preregulates said fluid from said supply pressure to a substantially constant preregulated pressure supplied to said primary regulator for said selected period of time; and
- a distribution device, coupled to an output of said primary regulator, selectively distributing said fluid at said substantially constant and precisely regulated pressure to said container.

50. The pressure injection apparatus as defined in claim 49 further including:

digital control means operably coupled to said primary regulator for digital operation thereof.

51. The pressure injection apparatus as defined in claim 49 further including:

analog control means operably coupled to said primary regulator for analog operation thereof.

52. The pressure injection apparatus as defined in claim 49 wherein, said distribution device includes a three-way valve device.

53. The pressure injection apparatus as defined in claim 49 further including:

a fixed pressure regulator, coupled in series between said output of said supply source and an input of said secondary regulator, that regulates said fluid at said supply pressure to a generally constant pressure supplied to said secondary regulator.

54. The pressure injection apparatus as defined in claim 53 wherein, said supply source is formed to output said supply pressure between about 20 psi and about 50 psi, said fixed pressure regulator is formed to regulate said generally constant pressure at about 15 psi, said servo pressure secondary regulator is formed to regulate said preregulated pressure to between about 0 psi and about 8 psi, and said servo pressure primary regulator is formed to regulate said substantially constant regulated pressure to between about 0 psi and about 2.5 psi.

55. The pressure injection apparatus as defined in claim 49 wherein, the secondary gain of said secondary regulator, from a command voltage to preregulated pressure, is substantially proportional to the primary gain of said primary regulator, from said command voltage to said regulated pressure such that said secondary regulator tracks said primary regulator to enable a substantially constant ratio between said preregulated pressure and said regulated pressure.

56. The pressure injection apparatus as defined in claim 49 wherein, said servo pressure primary regulator includes:

a first pressure sensor outputting a first feedback signal proportional to real time measurement of the regulated pressure;

a first reference source outputting a first command signal having a value representing a predetermined first command pressure;

a first computer coupled to receive as inputs said first feedback signal and said first command signal, and outputting a first compensation signal in response to a first difference between said first feedback signal and said first command signal; and a first valving assembly, responsive to said first compensation signal and in communication with the fluid, formed to adjust said regulated pressure to be substantially equal to said first command pressure such that a magnitude of the first difference between said first feedback signal and said first command signal is reduced.

57. The pressure injection apparatus as defined in claim 36 wherein, said first valving assembly includes:

a first vent valve responsive to said first compensation signal, and controllably movable between a closed position and an opened position, controllably venting the fluid to reduce said regulated pressure thereof; and a first inlet valve responsive to said first compensation signal, and controllably movable between a shut position and an unshut position, enabling fluid communication of the fluid at the supply pressure with the fluid at the regulated pressure to increase said regulated pressure.

58. The pressure injection apparatus as defined in claim 57 wherein, said first computer includes a first valve controller coupled to said first vent valve and said first inlet valve for controlled operation of said first vent valve between said closed position and said opened position, and of said first inlet valve between said shut position and said unshut position.

59. The pressure injection apparatus as defined in claim 58 wherein, said first vent valve and said first inlet valve are proportional microvalves.

60. The pressure injection apparatus as defined in claim 56 wherein, a first pressure sensor is provided by a pressure transducer.

61. The pressure injection apparatus as defined in claim 56 wherein, said first computer is formed to output said first compensation signal upon the absolute of said first difference between said first feedback signal and said first command signal exceeding a predetermined amount, representing a predetermined differential pressure.

62. The pressure injection apparatus as defined in claim 61 wherein, said first computer is formed to output said first compensation signal when said predetermined differential pressure is between about 0.001 psi to about 0.005 psi.

63. The pressure injection apparatus as defined in claim 56 wherein, said secondary regulator includes:

a second pressure sensor outputting a second feedback signal proportional to real time measurement of the preregulated pressure;

a second reference source outputting a second command signal having a value representing a predetermined second command pressure;

a second computer coupled to receive as inputs said second feedback signal and said second command signal, and outputting a second compensation signal in response to a second difference between said second feedback signal and said second command signal; and a second valving assembly, responsive to said second compensation signal and in communication with the fluid, and formed to adjust said preregulated pressure to be substantially equal to said second command pressure such that a magnitude of said second difference is reduced.

64. The pressure injection apparatus as defined in claim 63 wherein, said first valving assembly includes a first vent valve responsive to said first compensation signal, and controllably movable between a closed position and an opened position, controllably venting the fluid in communication with said primary servo regulator to reduce said regulated pressure thereof, and a first inlet valve responsive to said first compensation signal, and controllably movable between a shut position and an unshut position, enabling communication of the fluid at the preregulated pressure with the fluid at the regulated pressure to increase said regulated pressure thereof, and said second valving assembly includes a second vent valve responsive to said second compensation signal, and controllably movable between a closed condition and an opened condition, controllably venting the fluid to reduce said preregulated pressure thereof, and a second inlet valve responsive to said second compensation signal, and controllably movable between a shut condition and an unshut condition, enabling communication of the fluid at the supply pressure with the fluid at the preregulated pressure to increase said preregulated pressure thereof.

65. The pressure injection apparatus as defined in claim 64 wherein, said first computer further includes a first valve controller coupled to said first vent valve and said first inlet valve for controlled operation of said first vent valve between said closed position and said opened position, and of said first inlet valve between said shut position and said unshut position, and said second computer includes a second valve controller coupled to said second vent valve and said second inlet valve for controlled operation of said second vent valve between said closed condition and said opened condition, and of said first inlet valve between said shut condition and said unshut condition.

66. The pressure injection apparatus as defined in claim 65 wherein, said first vent valve, said first inlet valve, said second vent valve, and said second inlet valve are proportional microvalves.

67. The pressure injection apparatus as defined in claim 64 wherein said first computer includes a first valve controller coupled to said first vent valve and said first inlet valve for controlled operation of said first vent valve between said closed position and said opened position, and of said first inlet valve between said shut position and said unshut position;

said second computer further includes a second valve controller coupled to said second vent valve and said second inlet valve for controlled operation of said second vent valve between said closed condition and said opened condition, and of said second inlet valve between said shut condition and said unshut condition.

68. The pressure injection apparatus as defined in claim 67 further including:

a command controller operably coupled to said first computer and said second computer, and outputting a control signal for control of said first computer and said second computer simultaneously.

69. The pressure injection apparatus as defined in claim 68 further including:

a user interface coupled to said command controller to selectively vary said control signal.

70. The pressure injection apparatus as defined in claim 68 wherein, said substantially constant ratio is between about 2:1 to about 3:1.

71. The pressure injection apparatus as defined in claim 63 wherein, said first computer is formed to output said first compensation signal upon the absolute of said first difference between said first feedback signal and said first command signal exceeding a first predetermined amount, representing a first predetermined differential pressure, and said second computer is formed to output said second compensation signal upon the absolute of said second difference between said second feedback signal and said second command signal exceeding a second predetermined amount, representing a second predetermined differential pressure.

72. The pressure injection apparatus as defined in claim 71 wherein, said first computer is formed to output said first compensation signal when said first predetermined differential pressure is between about 0.001 psi to about 0.005 psi, and said second computer is formed to output said second compensation signal when said second predetermined differential pressure is between about 0.001 psi to about 0.005 psi.

73. The pressure injection apparatus as defined in claim 60 wherein, said secondary regulator includes a secondary accumulator, coupled in series between the output of said secondary regulator and an input of said primary regulator, having an internal cavity at said substantially constant preregulated pressure.

74. The pressure injection apparatus as defined in claim 60 wherein, said primary regulator includes a primary accumulator, coupled in series between the output of said primary regulator and an input of said distribution device, having an internal reservoir at said substantially constant regulated pressure.

75. The pressure injection apparatus as defined in claim 74 wherein, said internal reservoir has a volume of at least 1 cubic inch.

76. The pressure injection apparatus as defined in claim 74 wherein, said internal reservoir has a volume of at least about 1 cubic inch, and said internal cavity has a volume of at least about 1 cubic inch.

77. A method for injecting a quantitatively defined volume of liquid sample from a container into a capillary device comprising the steps of:

supplying a pressurized fluid at a supply pressure;

precisely preregulating said fluid from said supply pressure to a substantially constant preregulated pressure through a servo pressure secondary regulator by:

outputting a second feedback signal, from a secondary pressure sensor, proportional to real time measurement of the preregulated pressure;

outputting a second command signal, from a secondary reference source, having a value representing a predetermined second command pressure;

comparing said second feedback signal and said second command signal through a second computer, and outputting a second compensation signal in response to a second difference between said second feedback signal and said second command signal; and adjusting said preregulated pressure, through a secondary valving assembly responsive to said second compensation signal and in communication with the fluid, to be substantially equal to said second command pressure such that a magnitude of said second difference is reduced;

precisely regulating said fluid from said supply pressure to a substantially constant regulated pressure through a servo pressure primary regulator by:

outputting a first feedback signal, from a pressure sensor, proportional to real time measurement of the regulated pressure;

outputting a first command signal, from a first reference source, having a value representing a predetermined first command pressure;

comparing said first feedback signal and said first command signal through a first computer, and outputting a first compensation signal in response to a first difference between said first feedback signal and said first command signal; and adjusting said regulated pressure, through a valving assembly responsive to said first compensation signal and in communication with the fluid, to be substantially equal to said command pressure such that a magnitude of said first difference is reduced; and selectively exposing said liquid sample contained in said container to said fluid at said substantially constant and precisely regulated pressure for a predetermined period of time to inject the defined volume of said liquid sample from said container into said capillary device.

78. The method as defined in claim 77 wherein, said preregulating step includes tracking the secondary gain of said secondary regulator to be substantially proportional to the primary gain of said primary regulator to enable a substantially constant ratio between said preregulated pressure and said regulated pressure.

79. A pressure injection apparatus that injects a quantitatively defined volume of liquid sample from a container into a capillary device, said pressure injection apparatus comprising:

a container;

a capillary device;

a supply source of pressurized fluid at a supply pressure to urge said liquid sample an input of said capillary device;

a servo pressure regulator, coupled in series between an output of said supply and an input of said capillary device, that precisely regulates said fluid from said supply pressure to a substantially constant regulated pressure for a selected period of time, said servo pressure regulator including:

a pressure sensor outputting a feedback signal proportional to real time measurement of the regulated pressure;

a reference source outputting a command signal having a value representing a predetermined command pressure;

a computer coupled to receive as inputs said feedback signal and said command signal, and outputting a compensation signal in response to a difference between said feedback signal and said command signal; and a valving assembly, responsive to said compensation signal and in communication with the fluid, formed to adjust said regulated pressure to be substantially equal to said command pressure such that a magnitude of the difference between said feedback signal and said command signal is reduced, said valving assembly including:

a vent proportional microvalve responsive to said compensation signal, and controllably movable between a closed position and an opened position, controllably venting the fluid to reduce said regulated pressure thereof; and an inlet proportional microvalve responsive to said compensation signal, and controllably movable between a shut position and an unshut position, enabling fluid communication of the fluid at the supply pressure with the fluid at the regulated pressure to increase said regulated pressure, said computer including a valve controller coupled to the vent microvalve and the inlet microvalve for controlled operation of the vent microvalve between said closed position and said opened position, and of the inlet microvalve between said shut position and said unshut position; and a distribution device, coupled to an of said servo pressure regulator, selectively distributing said fluid at said substantially constant and precisely regulated pressure to said container.

* * * * *

UNITED STATES PATENT AND TRADEMARK OFFICE
CERTIFICATE OF CORRECTION

PATENT NO. : 5,667,657
DATED : September 16, 1997
INVENTOR(S) : RECKNOR et al.

It is certified that error appears in the above-identified patent and that said Letters Patent is hereby corrected as shown below:

Column 5, line 32, delete "device 23" and insert therefor --device 32---.

Column 12, line 17, delete "(DIONEXAD-20)" and insert therefor --(DIONEX AD-20)---.

Column 13, line 55, Claim 6, delete "skid" and insert therefor --said---.

Column 16, line 49, Claim 20, delete "the at the" and insert therefor --the fluid at the---.

Column 17, line 39, Claim 25, delete "commend" and insert therefor --command---.

Column 17, line 63, Claim 28, delete "end" and insert therefor --and---.

Column 17, line 66, Claim 28, delete "position said" and insert therefor --position and said---.

Column 18, line 66, Claim 37, delete "applied" and insert therefor --supplied---.

Column 19, line 33, Claim 40, delete "32" and insert therefor --37---.

Column 19, line 34, Claim 40, delete "connected" and insert therefor --coupled---.

Column 19, line 37, Claim 41, delete "31" and insert therefor --37---.

Column 21, line 53, Claim 57, delete "36" and insert therefor --56---.

UNITED STATES PATENT AND TRADEMARK OFFICE
CERTIFICATE OF CORRECTION

PATENT NO. : 5,667,657
DATED : September 16, 1997
INVENTOR(S) : RECKNOR et al.

It is certified that error appears in the above-identified patent and that said Letters Patent is hereby corrected as shown below:

Column 24, line 14, Claim 73, delete "60" and insert therefor --49---.

Column 24, line 21, Claim 74, delete "60" and insert therefor --49---.

Column 25, line 34, Claim 79, delete "sample an" and insert therefor --sample into an---.

Column 25, line 37, Claim 79, delete "supply and" and insert therefor --supply source and---.

Column 26, line 36, Claim 79, delete "an of" and insert therefor --an output of---.

Signed and Sealed this

Seventh Day of July, 1998

*Attest:*

BRUCE LEHMAN

*Attesting Officer*   Commissioner of Patents and Trademarks